US00PP16697P2

(12) United States Plant Patent
Evers

(10) Patent No.: US PP16,697 P2
(45) Date of Patent: Jun. 20, 2006

(54) HYBRID TEA ROSE PLANT NAMED 'TAN97544'

(50) Latin Name: *Rosa hybrida*
Varietal Denomination: TAN97544

(75) Inventor: Hans Jürgen Evers, Oetersen (DE)

(73) Assignee: Rosen Tantau Mathias Tantau Nachfolger, Uetersen (DE)

( * ) Notice: Subject to any disclaimer, the term of this patent is extended or adjusted under 35 U.S.C. 154(b) by 69 days.

(21) Appl. No.: 10/926,431

(22) Filed: Aug. 24, 2004

(51) Int. Cl.
*A01H 5/00* (2006.01)

(52) U.S. Cl. ..... Plt./131

(58) Field of Classification Search ..... Plt./131
See application file for complete search history.

(56) References Cited

PUBLICATIONS

Upov–Rom Plant Variety Database 2005/01 for cited 'TAN97544'.*

* cited by examiner

*Primary Examiner*—Anne Marie Grunberg
*Assistant Examiner*—Annette H Para
(74) *Attorney, Agent, or Firm*—Klarquist Sparkman LLP

(57) ABSTRACT

Hybrid tea rose plant having upright growth, long flower stems and long vase life.

1 Drawing Sheet

Figure 1:
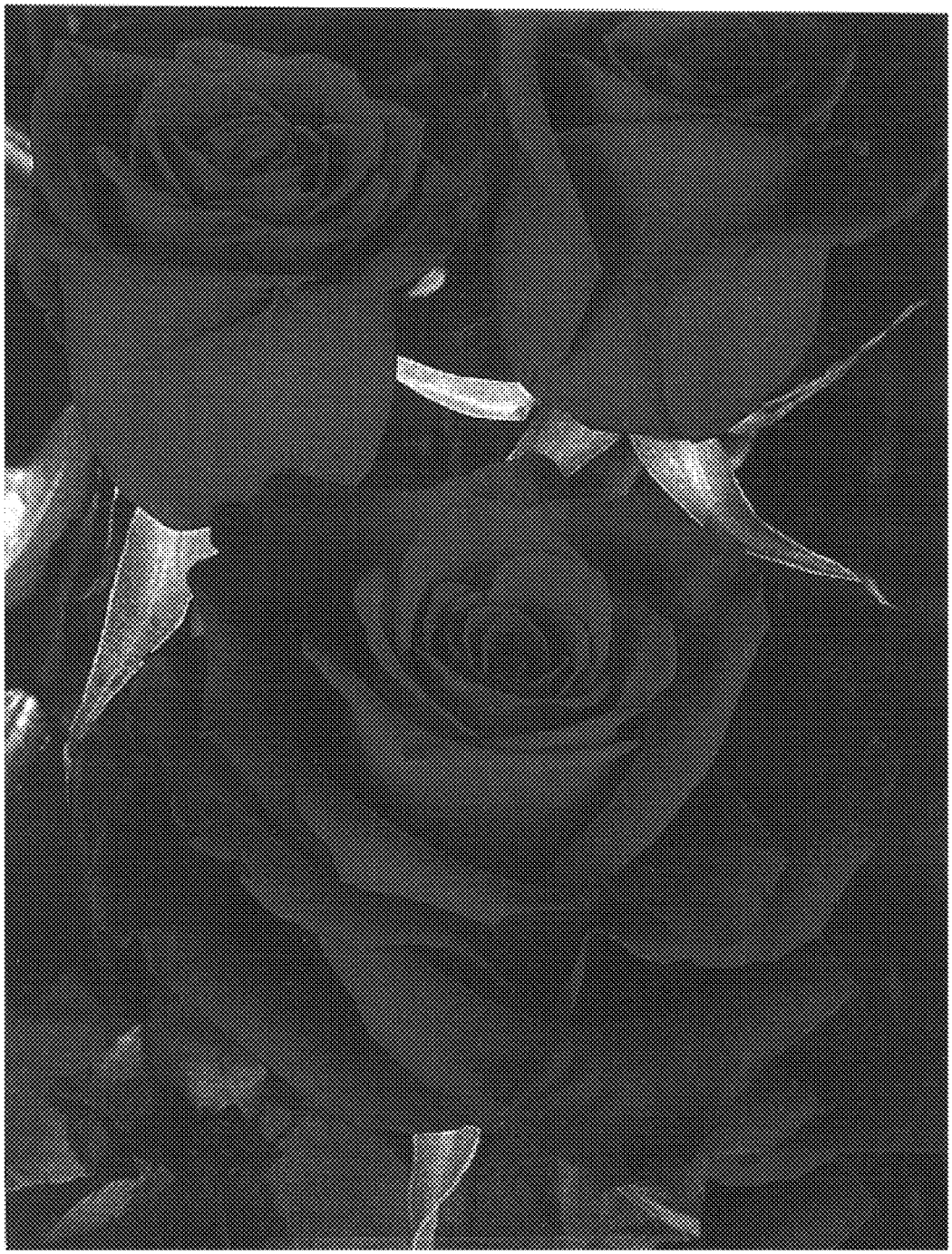

Genus and species: *Rosa hybrida.*
Varietal denomination: 'TAN97544'.

SUMMARY OF THE INVENTION

The present invention relates to a new and distinct variety of hybrid tea rose plant named 'TAN97544', which was originated by me by crossing an unnamed, unpatented variety with 'TANettola', U.S. Plant Pat. No. 11,020.

BACKGROUND OF THE INVENTION

The primary objective of this breeding was to produce a new rose variety for cut flower production having long stems, high production of flowers and long vase life.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Very upright plant.
2. Long stems.
3. Long vase life.

Asexual reproduction of this new variety by grafting as performed at Uetersen, Germany, shows that the foregoing and all other characteristics and distinctions come true to form and are established and transmitted through succeeding propagations.

Comparison with Parents

'TAN97544' has longer stems than the pollen parent and flowers of a darker color than the seed parent.

Comparison with Similar Variety

'TAN97544' is similar to the variety 'TANsaras' but has longer stems than 'TANsaras'.

BRIEF DESCRIPTION OF THE ILLUSTRATION

The accompanying illustration shows flowers of this new variety, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart (1966), except where ordinary dictionary significance of color is indicated.

Parentage:
*Seed parent.*—Unnamed variety.
*Pollen Parent.*—'TANettola', U.S. Plant Pat. No. 11,020.

FLOWER

Observations made from plants of fourteen months of age grown in a greenhouse environment at Uetersen, Germany.

Blooming habit: Continuous.
Bud:
*Size.*—About 4.8 cm long and 4.2 cm in diameter long when the petals start to unfurl.
*Form.*—The bud form is blunt.
*Color.*—When sepals first divide, bud color is Red Group 45B. When half blown, the upper and lower sides of the petals are Red Group 45A.
*Sepals.*—Color: Upper surface: Green Group 142A. Lower surface: Green Group 142C. Length: 4.6 cm.

Width: 1.2 cm. Shape: Pointed. Surface texture: Smooth. There are five normally appendaged sepals. There are five unappendaged sepals with smooth edges.

*Receptacle.*—Color: Green Group 140B. Shape: Funnel. Size: Small, 0.8 cm in diameter.

*Peduncle.*—Length: Medium, averaging about 7 cm. Surface: Smooth. Color: Green Group 140B. Strength: Stiff.

Bloom:

*Size.*—Large. Average open diameter is about 5.7 cm.

*Borne.*—Singly.

*Stems.*—Strength: Strong. Average length is about 70 cm and diameter about 0.6 cm.

*Form.*—When first open: Cupped. Permanence: Outer petals curl back.

*Petalage.*—Number of petals under normal conditions: 28.

*Color.*—The upper sides of the petals are Red Group 45A. The reverse sides of the petals are Red Group 46D. The base of each petal has a small yellow spot. The major color on the upper side is Red Group 45A.

*Variegations.*—None.

*Discoloration.*—The general tonality at the end of the first day: Red Group 45A.

*Fragrance.*—None.

Petals:

*Texture.*—Leathery, thin.

*Surface.*—Smooth.

*Shape.*—Heart-shaped.

*Size.*—Width: 5.8 cm. Length: 5 cm.

*Margin.*—Slightly curled back. Apex Shape: Pointed. Base Shape: Blunt.

*Form.*—Edges slightly quilled.

*Arrangement.*—Informal.

*Petaloids.*—Number: 8. Color: Red Group 45A.

*Persistence.*—Petals hang on and dry.

*Lastingness.*—On the plant: Very long, about 18 days. As a cut flower: Long, about 15 days.

Reproductive parts:

*Stamens.*—Number: 97. Length: 1.1 cm. Anthers: Length: 0.1 cm. Color: Yellow-Orange Group 168C. Arrangement: Regular around styles. Filaments: Color: Red Group 181C. Pollen: Color: Yellow Group 162B.

Pistils: Number: 89. Length: 1.2 cm. Styles: Color: Orange-Red Group 32A. Stigmas: Color: Orange Group 24A.

*Hips.*—None produced.

PLANT

*Form.*—Upright with erect stems.

*Growth.*—Vigorous.

*Mature plant.*—Height: 90 cm. at 2 years. Width: 35 cm.

*Rootstock.*—*Rosa canina* Inermis.

Foliage: Number of leaflets on normal mid-stem leaves: 7 .

*Size.*—Large (16 cm long×11.4 cm wide).

*Quantity.*—Normal.

*Color.*—New foliage: Upper side: Green Group 141A. Lower side: Green Group 139C. Old foliage: Upper side: Green Group 141A. Lower side: Green Group 141B.

Leaflets:

*Size.*—About 6.6 cm long×4.7 cm wide.

*Shape.*—Pointed oval.

*Base shape.*—Blunt.

*Apex shape.*—Blunt.

*Texture.*—Upper side: Leathery.

*Edge.*—Serrated.

*Serrations.*—Single.

*Petiole.*—Color: Green Group 139D.

*Petiole rachis.*—Color: Green Group 139C. Underside: Smooth.

*Stipules: Smooth. Length:* 3 cm.

*Auricles.*—None present.

*Disease resistance.*—Resistant to powdery mildew and blackspot. No information available on resistance to rust. Growing conditions: Greenhouse.

*Pest resistance.*—Not tested.

*Vein color.*—Green Group 141D.

*Venation pattern.*—Pyramidal.

Wood:

*New wood.*—Color: Green Group 141B. Bark: Smooth.

*Old wood.*—Color: Greyed-Purple Group 183B. Bark: Rough.

Prickles:

*Quantity.*—On main canes from base: Ordinary, 7 per internode. On laterals from main canes: Few.

*Form.*—Hooked downward.

*Length.*—1.1 cm.

*Color when young.*—Green Group 153A.

*Color when mature.*—Greyed-Orange Group 177B.

Small prickles:

*Quantity.*—On main stalks: Few. On laterals: Four.

*Color when young.*—Green Group 153A.

*Color when mature.*—Greyed-Orange Group 177B.

Winter hardiness: Not tested.

I claim:

1. A new and distinct variety of rose plant of the hybrid tea class, substantially as herein shown and described, characterized particularly by its upright growth, long flower stems and long vase life.

* * * * *